United States Patent [19]

Young et al.

[11] Patent Number: 5,554,167
[45] Date of Patent: Sep. 10, 1996

[54] TISSUE PIERCING MEMBERS

[75] Inventors: Wayne P. Young, Brewster, N.Y.; Dominick L. Mastri, Bridgeport, Conn.; Henry Bolanos, East Norwalk, Conn.; George M. Chelednik, Bethel, Conn.

[73] Assignee: United States Surgical Corporation, Norwalk, Conn.

[21] Appl. No.: 280,686

[22] Filed: Jul. 26, 1994

Related U.S. Application Data

[63] Continuation-in-part of Ser. No. 134,354, Oct. 8, 1993, Pat. No. 5,554,137.

[51] Int. Cl.⁶ .............................. A61B 17/32; A61M 5/18
[52] U.S. Cl. ....................... 606/184; 604/274; 604/164
[58] Field of Search .......................... 30/152, 162, 346, 30/335, 360, 349, 358, 366, 339 X, 337, 329; 604/274, 272, 174, 165, 164; 606/184–185, 166–167, 170–172; 401/117, 91; D24/147

[56] References Cited

U.S. PATENT DOCUMENTS

| | | |
|---|---|---|
| 1,380,447 | 6/1921 | Westcott . |
| 3,584,624 | 6/1971 | de Clutiis . |
| 4,414,974 | 11/1983 | Dotson et al. . |
| 4,499,898 | 2/1985 | Knepshield et al. . |
| 4,601,710 | 7/1986 | Moll . |
| 4,654,030 | 3/1987 | Moll et al. . |
| 4,723,545 | 2/1988 | Nixon et al. . |
| 5,066,288 | 11/1991 | Deniega et al. . |
| 5,116,353 | 5/1992 | Green . |
| 5,232,440 | 8/1993 | Wilk . |
| 5,314,417 | 5/1994 | Stephens et al. . |
| 5,342,382 | 8/1994 | Brinkerhoff et al. . |
| 5,364,372 | 11/1994 | Danks et al. . |
| 5,366,445 | 11/1994 | Haber et al. . |

FOREIGN PATENT DOCUMENTS

| | | |
|---|---|---|
| 0479565 | 4/1992 | European Pat. Off. . |
| 0604197 | 6/1994 | European Pat. Off. . |
| 4020956 | 1/1991 | Germany . |
| 921554 | 4/1982 | U.S.S.R. . |
| 1356386 | 6/1974 | United Kingdom . |

*Primary Examiner*—Gary Jackson
*Assistant Examiner*—Nancy Mulcare

[57] ABSTRACT

A piercing tip for penetrating body tissue is provided which includes a conical body and a triangular cutting blade positioned within a slot formed in the conical body. The cutting blade includes a proximal mounting flange which extends outwardly from the conical body and is configured for mounting at the distal end of an obturator of a trocar assembly.

20 Claims, 5 Drawing Sheets

TISSUE PIERCING MEMBERS

This is a continuation-in-part of U.S. application Ser. No. 08/134,354, filed Oct. 8, 1993, now U.S. Pat. No. 5,554,137, the contents of which are hereby incorporated by reference in their entirety.

BACKGROUND OF THE INVENTION

1. Technical Field

The present invention relates to tissue piercing members and to trocar assemblies which incorporate such tissue piercing members.

2. Description of the Related Art

Trocar assemblies are well known devices for piercing body walls so as to gain access to underlying structures. In the context of minimally invasive surgical and diagnostic procedures, e.g., laparoscopic, thoracoscopic and arthroscopic procedures, the trocar is utilized to facilitate introduction of a cannula or guide sleeve through the body wall. The cannula, once positioned, provides a port of entry for additional instrumentation, e.g., an endoscope, clip applier, scissors, graspers, retractors, and the like. Recently, the development of essential mechanical instrumentation for use through cannulae has enabled the widespread acceptance of numerous minimally invasive procedures.

In introducing the initial trocar/cannula assembly through the body wall, the surgeon generally has no visualization of the body cavity or the location of internal structures. To provide an increased margin of safety, trocars have been developed which provide mechanisms adapted to cover the piercing member upon entry into the body cavity, e.g., SU 921554 to Markelov, U.S. Pat. No. 4,601,710 to Moll et al. and U.S. Pat. No. 5,116,353 to Green.

In utilizing trocar/cannula assemblies, the surgeon's control during entry is at least in part predicated on the penetration force required to pass the trocar through the body wall. The lower the force required, the more control the surgeon will have during entry. Thus, for example, U.S. Pat. No. 4,654,030 to Moll et al. provides a safety shielded trocar in which the safety shield is designed to minimize the trocar's penetration force. A variety of trocar piercing tip designs have also been disclosed, e.g., pyramidal and conical tips. U.S. Pat. No. 1,380,447 to Westcott discloses a trocar which includes a perforator or blade having a sharp tapered point and two sharp cutting edges. See also U.S. Pat. No. 4,499,898 to Knepshield et al. (surgical knife with controllably extendable blade), U.S. Pat. No. 3,584,624 to de Clutiis (catheter which receives rigid stylet with a cutting edge), U.S. Pat. No. 4,414,974 to Dotson et al. (microsurgical knife), U.S. Pat. No. 5,232,440 to Wilk (assembly for draining abscesses) and U.K. 1,356,386 to Moss et al. (artery entry tool). The design of the trocar's piercing tip will also influence the degree to which tissue is traumatized during trocar entry.

A need thus exists for a piercing tip design which maximizes the surgeon's control during trocar entry by reducing penetration force and which minimizes tissue trauma.

SUMMARY

A piercing tip is provided which is particularly adapted for use with trocar assemblies. The piercing tip minimizes penetration force and tissue trauma and is economical in manufacture, reducing the manufacturing cost of trocar assemblies relative to prior art trocar piercing tip designs.

More particularly, the piercing tip of the invention includes a conical body which defines an outer face and a base of circular cross-section. The piercing tip also includes a substantially planar cutting blade having a triangular cutting region. The cutting blade is positioned within a slot formed in the conical body such that the triangular cutting region extends at least in part beyond the outer face of the conical body. In a preferred embodiment, the conical body includes a cylindrical extension which projects from the circular base and an outwardly extending projection which is adapted to mount the conical body to an obturator. In a further preferred embodiment, the conical body is formed from first and second body portions and the slot is formed in a region intermediate these two body portions.

The invention also provides a trocar which includes an obturator defining a longitudinal axis, and a conical piercing tip body mounted to the obturator. The conical piercing tip body defines an outer face and a base of circular cross-section which is transverse to the obturator's longitudinal axis. The trocar also includes a substantially planar cutting blade having a triangular cutting region. The cutting blade is positioned within a slot formed in the conical body such that the triangular cutting region extends at least in part beyond the outer face of the conical body.

In another preferred embodiment of the present invention, a piercing tip may be provided with a substantially planar cutting blade which is configured to directly mount to an obturator. The cutting blade includes a proximal mounting flange projecting outwardly from the conical body so as to mount to a distal end of an obturator.

BRIEF DESCRIPTION OF THE DRAWINGS

The features and advantages of the present invention will become apparent from consideration of the following specification when taken in conjunction with the accompanying drawings in which.

DETAILED DESCRIPTION OF PREFERRED EMBODIMENTS

Figure 1:
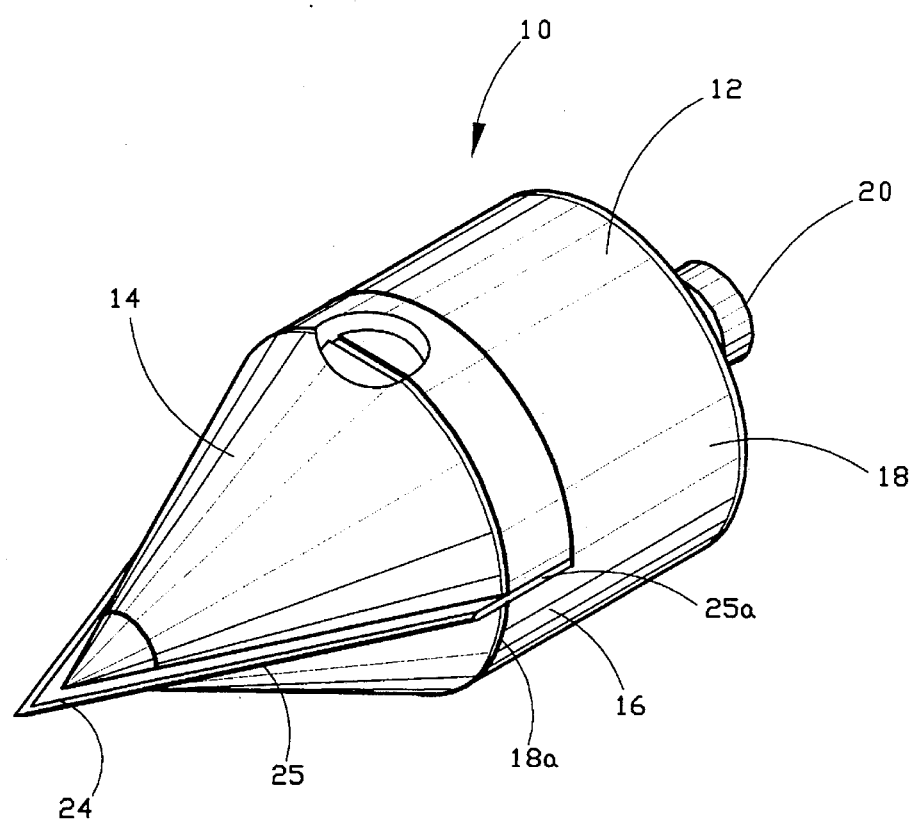
FIG. 1 is a perspective side view of a piercing tip according to the present invention.
Figure 2:
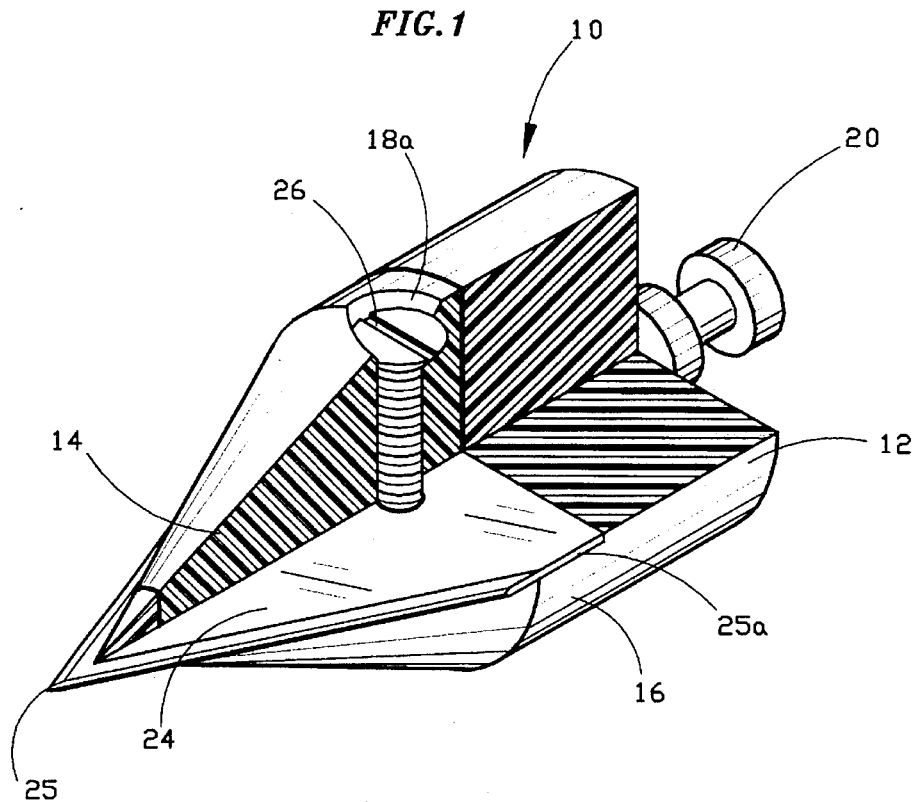
FIG. 2 is a perspective side view, partially in section, of the piercing tip of FIG. 1.
Figure 3:
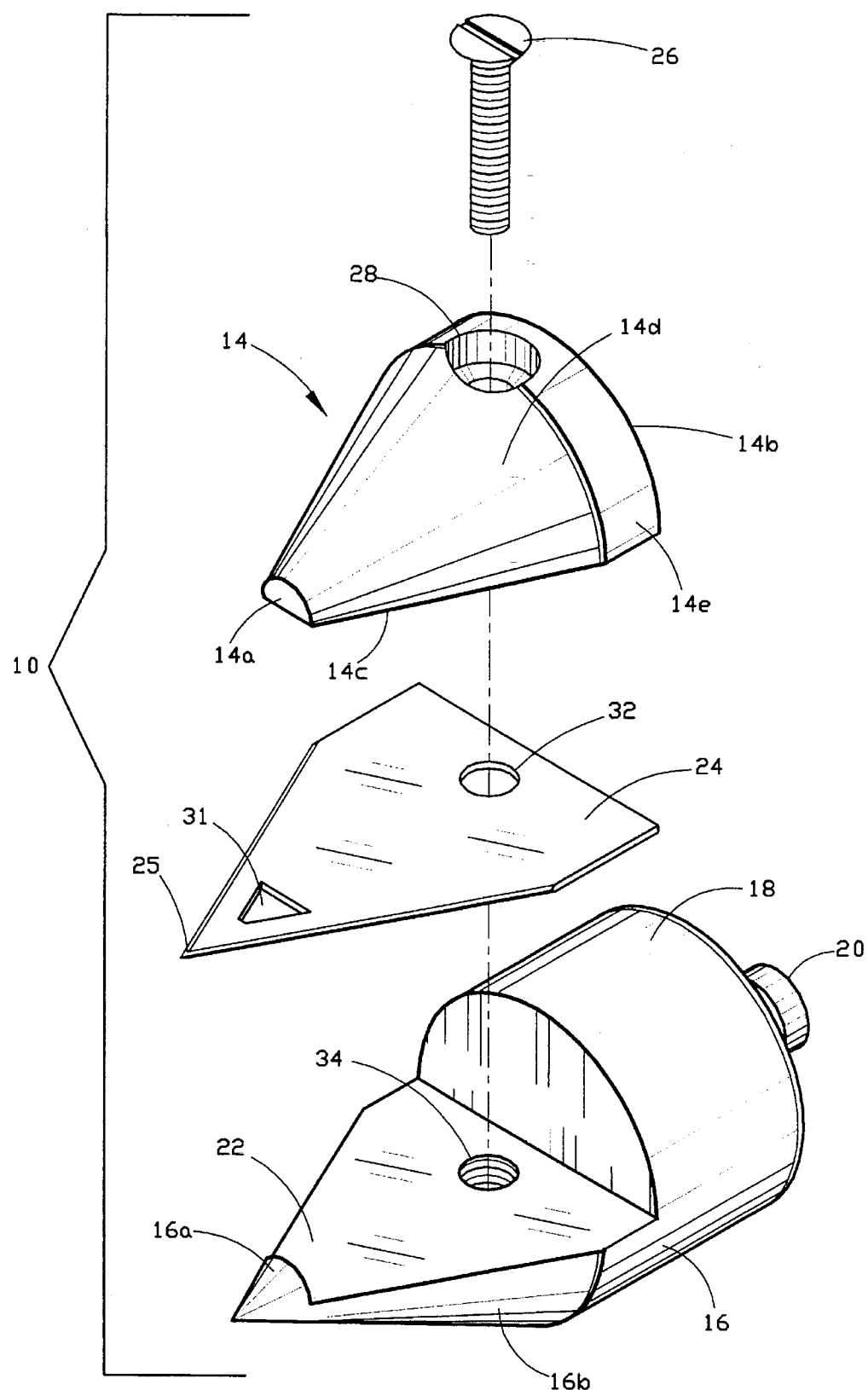
FIG. 3 is an exploded perspective view, with parts separated, of the piercing tip.

Referring to FIGS. 1–3, piercing tip 10 includes a body 12 which is formed by two body portions 14, 16. Body portion 14 defines a distal face 14a, a proximal face 14b, a planar side wall 14c, a non-planar side wall 14d having a longitudinal cross-sectional dimension that varies axially therealong and a curved portion 14e preferably having a uniform cross-section dimension axially therealong. Body portion 16 defines a distal conical portion 16a, an intermediate partial frustoconical portion 16b and a proximal cylindrical extension 18. Body portion 14 is adapted to cooperate with and receive the intermediate partial frustoconical portion 16b of body portion 16 such that when body portions 14 and 16 are assembled, as shown in FIG. 1, body 12 is conically configured at its distal end and includes cylindrical extension 18 at its proximal end. An outwardly extending projection 20 extends proximally from cylindrical extension 18 and is adapted to be mounted to an obturator 31 (FIG. 5).

Figure 4:
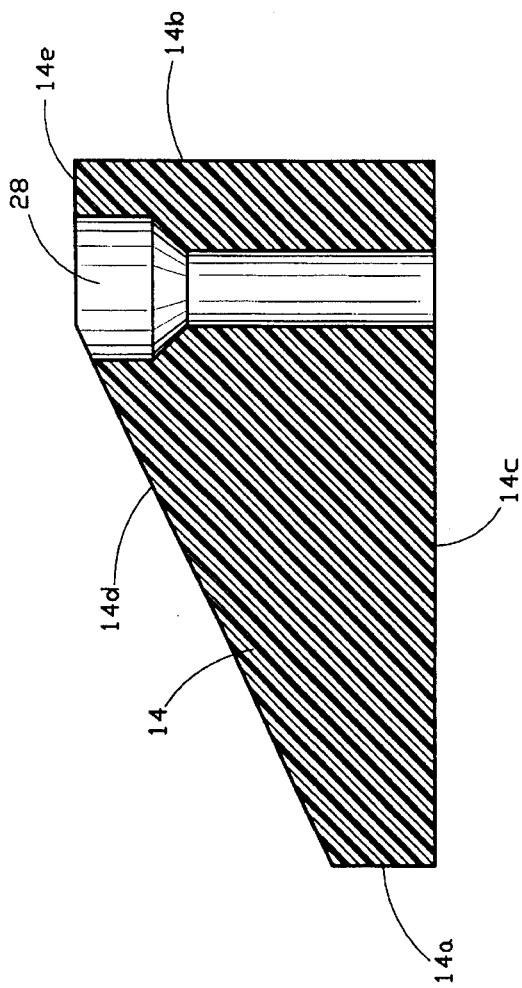
FIG. 4 is a sectional side view of a first body portion of the present invention.

A slot 22 is formed between body portions 14, 16 within which is mounted a substantially planar cutting blade 24. Slot 22 is transverse to the base 18a of cylindrical extension 18 and generally passes through the vertex defined by conical body 12. Cutting blade 24 includes a triangular distal portion and a substantially rectangular proximal portion. An aperture 31 is formed in the triangular distal portion of cutting blade 24 to receive the distal conical portion 16a of body portion 16. A screw 26 is passed through aperture 28 formed in body portion 14 (see FIG. 4), aperture 32 formed in cutting blade 24 and into aperture 34 formed in body portion 16 to secure cutting blade 24 to body 12. Of course, alternative means may be used to secure cutting blade 24 to body 12, as for example a dowel or pin. An adhesive may also be employed, either as a sole means of securement or in combination with other securement means. It is also contemplated that one or more molded keys or protrusions may be formed in body portion(s) 14 and/or 16 which may cooperate with apertures formed in cutting blade 24 to align and secure cutting blade thereto.

Figure 5:
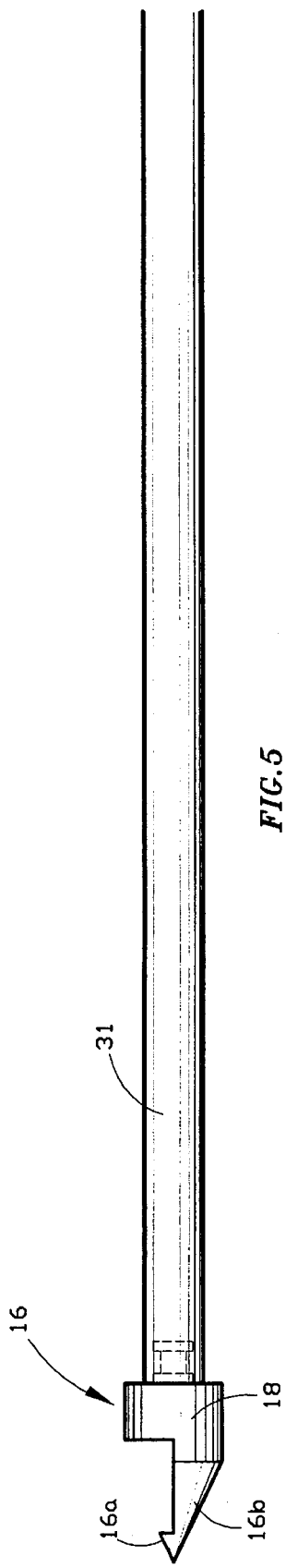
FIG. 5 is a side view of a piercing tip of the invention mounted to an obturator.

As shown in FIG. 5, piercing tip 10 is typically mounted to an obturator 31. The obturator 31 is adapted to be received in a cannula for introduction into a body cavity. Additional structures may be included as part of the trocar assembly, as is well known in the art, e.g. a valve mechanism, a desufflation lever, obturator and cannula housings, and the like. See, e.g., U.S. Pat. No. 5,116,353 to Green and U.S. Pat. No. 4,6601,710 to Moll, the contents of which are hereby incorporated by reference.

Cutting blade 24 projects beyond body portion 12 to provide an exposed triangular cutting edge 25 which incises the body wall and cuts through the tissue layers therebelow. Preferably, the triangular cutting edge 25 defines an isosceles triangle. Body portion 12 follows therebehind, dilating the body wall and tissue layers so as to facilitate introduction of the cannula. In a preferred embodiment, side face 25a of cutting edge 25 substantially aligns with the outer edge of cylindrical extension 18. By aligning side face 25a of cutting edge 25 with cylindrical extension 18, the degree to which the body wall and underlying tissue layers are cut is limited to the diameter of cylindrical projection 18. It is further contemplated that side face 25a may be recessed within cylindrical extension 18, thereby relying on the dilative function of the conically configured body portions 14, 16 to expand the incision to accommodate passage of the cannula into the body cavity.

Body portions 14, 16 are typically molded from a suitable polymer, e.g., Lexan, ABS or the like. Cutting blade 24 is fabricated from a material which will maintain a cutting edge, e.g., stainless steel.

Projection 20 is typically mounted in a cooperating socket formed at a distal end of an obturator 31. Preferably, projection 20 is adapted to rotate within the obturator socket, thereby permitting piercing tip 10 to rotate with respect to the obturator 31. Such relative motion helps to reduce tissue trauma as the piercing tip 10 is introduced through the body wall because, as the surgeon applies force to the trocar assembly, there is a tendency to rotate one's wrist. Inasmuch as the piercing tip 10 is able to rotate with respect to the obturator, the piercing tip 10 remains rotationally fixed with respect to the body wall once the body wall engages and surrounds the piercing tip 10 during entry therethrough, thereby ensuring a relatively direct entry of the piercing tip 10 through the body wall.

Figure 6:
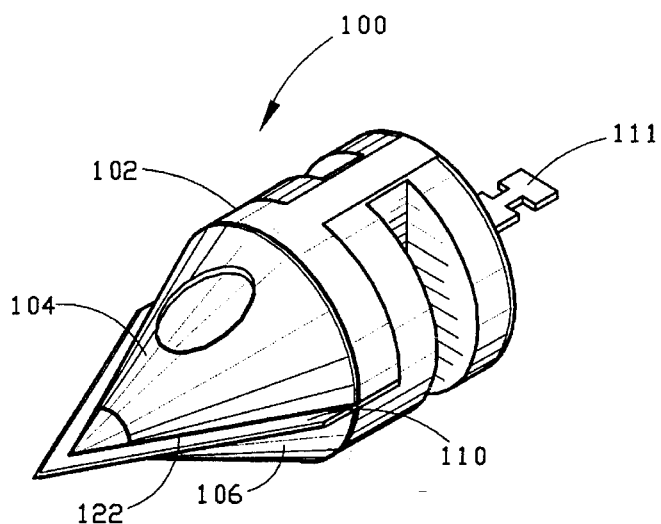
FIG. 6 is a perspective side view of a piercing tip according to another preferred embodiment of the present invention.

Another piercing tip in accordance with a preferred embodiment is illustrated in FIG. 6 and is designated generally by reference numeral 100. Piercing tip 100 is similar to piercing tip 10, described hereinabove, with the exception that the cutting blade 110 is configured to mount to the distal end of an obturator 150 (FIG. 8) so as to provide a direct connection between the obturator 150 and the cutting blade 110, thereby optimizing the transmission of force between the obturator 150 and the cutting blade 110 and further stabilizing cutting blade 110 relative to obturator 150.

Figure 7:
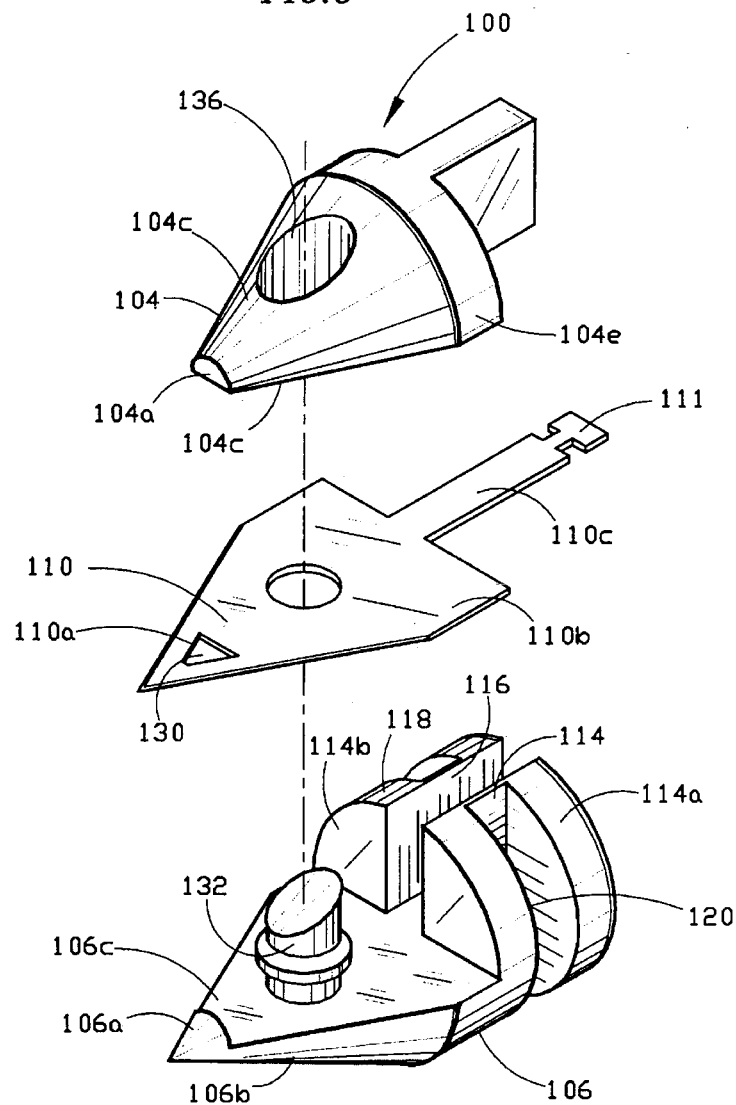
FIG. 7 is an exploded perspective view, with parts separated, of the piercing tip illustrated in FIG. 6.

Referring to FIGS. 6 and 7, the piercing tip 100 defines a longitudinal axis and includes a conical body 102 having an upper body member 104 and a lower body member 106. Further, the piercing tip 100 includes a cutting blade 110 which is mounted within the body 102, as described hereinbelow.

The upper body member 104 defines a distal face 104a, a proximal face 104b, a planar side wall 104c, a frustoconical sidewall 104d and a cylindrical portion 104e. The proximal face 104b has rectangular portion 104f extending longitudinally therefrom. The lower body member 106 defines a distal conical portion 106a and a proximal cylindrical extension 114. The proximal cylindrical extension 114 defines an elongated open channel 116 along the longitudinal axis of the piercing tip 100. The elongated open channel 116 is dimensioned and configured for reception of rectangular portion 104f of upper body member 104. Further, the outer cylindrical surface 114a of the proximal cylindrical extension defines first and second elongated cutouts 118 and 120 preferably formed parallel to one another and transverse to the longitudinal axis of the piercing tip 100. The upper body member 104 is configured to cooperate with and be received on the lower body member 106, for example, by snap fit or friction fit, such that when the body members 104 and 106 are assembled, as shown in FIG. 6, body 102 is conically configured at its distal end.

Figure 8:
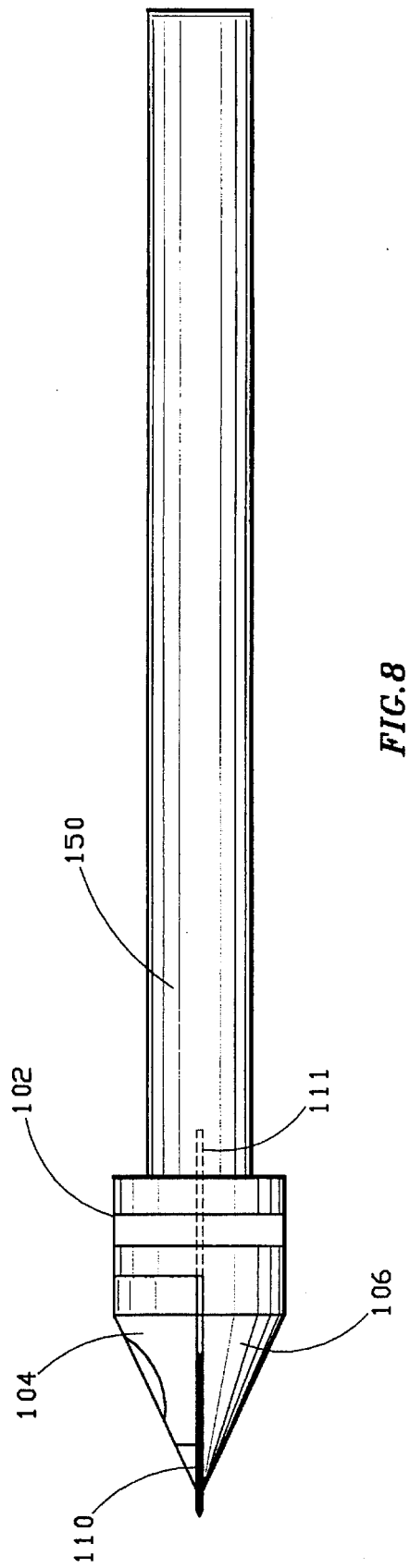
FIG. 8 is a side view of the piercing tip, illustrated in FIG. 6, mounted to an obturator.

A slot 122 is formed between the upper and lower body members 104 and 106, respectively, within which is mounted the substantially planar cutting blade 110. The slot 122 is formed transverse to the base 114b of the proximal cylindrical extension 114 and generally passes through the vertex defined by the conical body 102. The cutting blade 110 preferably includes a triangular distal portion 110a, a substantially rectangular intermediate portion 110b and an elongated proximal portion 110c. The elongated proximal portion 110c includes a mounting flange 111 which is configured to be received within the elongated open channel 116 of the lower body member 106 and project proximally from the conical body 102 of the piercing tip 100, as illustrated in FIG. 6. The mounting flange 111 of the elongated proximal portion 110c preferably defines a T-shaped configuration adapted to mount in a cooperating socket formed at a distal end of the obturator 150, as illustrated in FIG. 8. An aperture 130 is formed in the triangular distal portion of the cutting blade 110 configured to receive the distal conical portion 106a of the lower body member 106.

As best illustrated in FIG. 7, a mounting dowel 132 is provided on the lower body member 106 which projects upwardly from an intermediate planar portion 106c. Mounting dowel 132 is configured to pass through an aperture 134 formed in the cutting blade 110 and preferably snap-fit into an aperture 136 formed in the upper body member 104 so as to secure the cutting blade 110 to the body 102 of the piercing tip 100.

As shown in FIG. 8, the piercing tip 100 is configured to mount to an obturator 31, such that the proximal end 128 of the cutting blade 110 mounts within a cooperating socket formed at a distal end of the obturator 31.

While the invention has been particularly shown and described with reference to the preferred embodiments, it will be understood by those skilled in the art that various modifications and changes in form and detail may be made therein without departing from the scope and spirit of the invention.

What is claimed is:

1. A piercing tip for an obturator comprising:
   (a) a body member having a conical distal portion defining a longitudinal axis including a cylindrical portion which extends from a circular base of the body member having first and second elongated cutouts substantially parallel to one another and transverse to the longitudinal axis of the body member; and
   (b) a cutting blade associated with the body member including a distal edge portion extending beyond the periphery of the conical distal portion of the body member and a proximal mounting flange configured to mount the piercing tip to the obturator.

2. A piercing tip as recited in claim 1, wherein the cutting blade is a substantially planar cutting blade having a triangular cutting region, the cutting blade being positioned within a slot formed in the body member.

3. A piercing tip as recited in claim 2, wherein the body member defines an outer surface and a base of circular cross-section such that the slot is transverse to the base of the body member.

4. A piercing tip as recited in claim 2, wherein the proximal mounting flange of the cutting blade projects outwardly from the cylindrical extension.

5. A piercing tip as recited in claim 2, wherein the triangular cutting region defines an isosceles triangle and wherein the side walls of the isosceles triangle are substantially parallel to the outer surface of the conical distal portion of the body member.

6. A piercing tip as recited in claim 3, wherein the body member includes first and second body portions and the slot is formed in a region intermediate the first and second body portions.

7. A piercing tip as recited in claim 6, further including an attachment member extending from said second body portion adapted for securing the cutting blade to the body member.

8. A piercing tip as recited in claim 7, wherein the attachment member is selected from the group consisting of a screw, dowel, pin, molded protrusion, adhesive, and combinations thereof.

9. A piercing tip for an obturator comprising:
   (a) a body member having a conical distal portion defining a longitudinal axis, an outer surface and a base of circular cross-section such that a slot is transverse to the base of the body member and includes first and second body portions and the slot is formed in a region intermediate the first and second body portions, wherein the first body portion defines a distal face, a proximal face, a planar side wall and a non-planar side wall; and
   (b) A cutting blade associated with the body member including a distal edge portion extending beyond the periphery of the conical distal portion of the body member and a proximal mounting flange configured to mount the piercing tip to the obturator and is a substantially planar cutting blade having a triangular cutting region, the cutting blade being positioned within the slot formed in the body member.

10. A piercing tip as recited in claim 9, wherein the second body portion defines a distal conical portion, an intermediate partial frustoconical portion, and a proximal cylindrical portion and further wherein the first body portion cooperates with the intermediate partial frustoconical portion to define a conical body member.

11. A piercing tip as recited in claim 10, wherein the cutting blade defines an aperture which is adapted to receive the distal conical portion therethrough.

12. A piercing tip as recited in claim 9, wherein the body member includes a cylindrical portion which extends from a circular base of the body member.

13. A piercing tip as recited in claim 12, wherein the outer surface of the cylindrical portion defines first and second elongated cutouts substantially parallel to one another and transverse to the longitudinal axis of the body member.

14. A piercing tip as recited in claim 12, wherein the proximal mounting flange of the cutting blade projects outwardly from the cylindrical portion.

15. A piercing tip for an obturator comprising:
   (a) a body member having a distal conical portion and defining a longitudinal axis; said body member including:
      i) a first body portion defining a distal face, a proximal face a planar side wall and a non-planar side wall; and
      ii) a second body portion defining a distal conical portion, an intermediate partial frustoconical portion, and a proximal cylindrical portion, said second body being configured such that the first body portion cooperates with the intermediate partial frustoconical portion of the second body portion to define the distal conical portion;
   (b) a substantially planar cutting blade having a triangular cutting region and a proximal mounting flange at a proximal end portion, the cutting blade being positioned within a slot formed intermediate the first and second body portions such that the triangular cutting region extends at least in part beyond an outer surface of the distal conical surface and the proximal mounting flange extends outwardly from a proximal end of the body member so as to mount to the obturator; and
   (c) an attachment member for connecting the first body portion and the cutting blade to the second body portion.

16. A piercing tip as recited in claim 15, wherein the proximal end portion of the second body portion defines an elongated open channel along the longitudinal axis of the body member configured for reception of the proximal end portion of the cutting blade.

17. A piercing tip as recited in claim 16, further including a plug member extending from said first body portion configured for reception into the elongated open channel for securing the proximal end portion of the cutting blade within the body member.

18. A piercing tip as recited in claim 16, wherein the attachment member is a locking dowel extending from the second body portion so as to be received through an aperture defined in the cutting blade and the first body portion.

19. A piercing tip as recited in claim 16, wherein the proximal cylindrical portion of the second body portion defines first and second elongated cutout portions substantially parallel to one another and transverse to the longitudinal axis of the body member.

20. A piercing tip as recited in claim 16, wherein the cutting blade defines an aperture which is configured to receive the distal conical portion of the second body portion therethrough.

* * * * *